United States Patent [19]

Ishimatsu

[11] 3,954,617
[45] May 4, 1976

[54] APPARATUS FOR LIQUID CHROMATOGRAPHY HAVING AUTOMATIC SAMPLING SYSTEM

[75] Inventor: Toyohisa Ishimatsu, Toyonaka, Japan

[73] Assignee: Fujisawa Pharmaceutical Co., Ltd., Osaka, Japan

[22] Filed: Feb. 26, 1975

[21] Appl. No.: 553,352

[30] Foreign Application Priority Data

Feb. 27, 1974  Japan................................ 49-23085

[52] U.S. Cl............................................. 210/198 C
[51] Int. Cl.².......................................... B01D 15/08
[58] Field of Search................... 210/198 C; 55/197

[56] References Cited
UNITED STATES PATENTS

| | | | |
|---|---|---|---|
| 3,504,799 | 4/1970 | Ogle............................... | 210/198 C |
| 3,575,295 | 4/1971 | Yoshida et al.................. | 210/198 C |

Primary Examiner—John Adee
Attorney, Agent, or Firm—Allison C. Collard

[57] ABSTRACT

Apparatus for liquid chromatography having an automatic sampling system including an intermittently rotatable circular table having a number of sample cups on its peripheral portion, a wash liquor receptacle disposed close to the circular table, a withdrawing member reciprocally movable between the wash liquor receptacle and the sample cup brought to a specified position by the intermittent rotation of the circular table and then held in the position for a specified period of time to withdraw the samples and the wash liquor alternately, a sample supply tube having the withdrawing member connected thereto, a pump associated with the tube, and a sampling valve connected to the tube and communicating with a column. Different samples and wash liquor are alternately supplied to the sampling valve, which successively introduces the samples, each in a definite amount, to the column along with a developer.

6 Claims, 3 Drawing Figures

APPARATUS FOR LIQUID CHROMATOGRAPHY HAVING AUTOMATIC SAMPLING SYSTEM

BACKGROUND OF THE INVENTION

This invention relates to an apparatus for liquid chromatography having an automatic sampling system.

Generally microsyringes have heretofore been used to introduce a sample to the column of liquid chromatographic apparatus. The microsyringe is passed through a rubber septum provided at the inlet of the column every time the sample is to be injected into the column. When the septum is thus pierced with the microsyringe repeatedly, a hole is formed in the septum to permit the leakage of liquid. Consequently, there arises the problem that the amounts of samples involve wide variations. This is also attributable to the procedure in which the amounts of samples to be injected into the column are determined with the eyes. To overcome such problem, a liquid chromatograph equipped with a sampling valve has been developed. With this apparatus, the sample is manually injected into the inlet of the valve, which is manually operated to place a specified amount of sample into the column. However, the apparatus still necessitates a manual procedure, which makes it difficult to determine the amount with accuracy and efficiency.

SUMMARY OF THE INVENTION

To eliminate the foregoing drawbacks, the present invention provides an apparatus for liquid chromatography having an automatic sampling system which comprises an intermittently rotatable circular table having a number of sample cups on its peripheral portion, a wash liquor receptacle disposed close to the circular table, a sampling valve for intermittently introducing to a column different samples each in a definite amount and for introducing a developer into the column, and supply means for successively withdrawing the samples from the cups at regular intervals with the rotation of the circular table and for withdrawing a wash liquor from the receptable during the intervals to supply the samples and wash liquor alternately to the sampling valve, whereby the samples can be automatically supplied to the column. The apparatus therefore assures that the samples will be introduced into the column in accurate amounts and with efficiency.

DESCRIPTION OF THE PREFERRED EMBODIMENT

Figure 1:
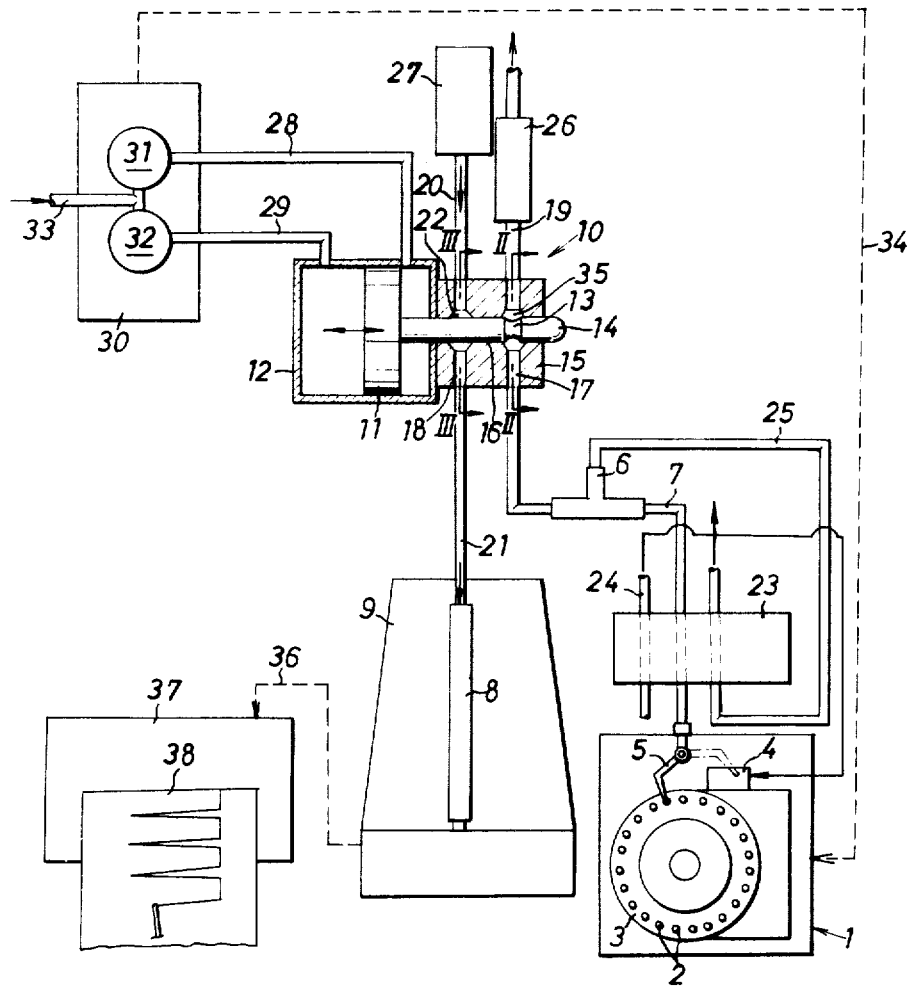
FIG. 1 is a schematic diagram showing an embodiment of this invention.

With reference to FIG. 1, a sampler 1 includes an intermittently rotatable circular table 3 which is provided on its peripheral portion with a number of sample cups 2. A wash liquor receptacle 4 is disposed close to the circular table 3. The sample 1 has a withdrawing member 5 automatically and reciprocally movable, by an unillustrated operating means, between the wash liquor receptacle 4 and the sample cup 2 brought to a specified position by the intermittent rotation of the circular table 3 and then held in that position for a specified period of time so as to pick up each of the samples and the wash liquor alternately. A stainless steel probe is used as the withdrawing member 5. Suitable for use as the wash liquor is distilled water containing a surface active agent or an organic solvent. The member 5 is connected to a sample supply tube 7 having a debubbler 6.

A liquid chromatography apparatus 9 including a column 8 incorporates therein a sampling valve 10. For a better understanding, the valve 10 is illustrated in the drawing as separated from the apparatus 9. The sampling valve 10 comprises a hydraulic cylinder 12 housing a piston 11, a piston rod 14 formed, in its peripheral surface close to the front end thereof, with an annular groove 13 for accommodating a definite amount of sample, and a body 15 fixed to the front end of the cylinder 12, with the piston rod 14 extending through the body 15. The body 15 has a rod bore 16 in which the rod is slidable, and a first passage 17 and a second passage 18 which are parallel to each other as spaced apart by a distance corresponding to the stroke of the rod 14 and which intersect the rod bore 16. Each of the passages 17 and 18 is in the form of a bore extending through the body 15 and has a diameter smaller than the diameter of the rod 14. The first passage 17 communicates with the sample supply tube 7 at one end and with a sample discharge tube 19 at the other end. The second passage 18 has one end communicating with a developer supply tube 20 and the other end communicating with a tube 21 in communication with the column 8. The inner surface of the body 15 defining the rod bore 16 is formed with liquid passing annular grooves 22 and 35 at the inter-sections of the rod bore 16 and the passages 17 and 18. A proportioning pump 23 is associated with the supply tube 7 to alternately withdraw each sample and wash liquor and force them into the first passage 17 in the sampling valve 10. A wash liquor replenishing tube 24 is connected to the wash liquor receptacle 4. An air release tube 25 is connected to the debubbler 6. The pump 23 is associated with the tubes 24 and 25. The sample discharge tube 19 is provided with a restrictor 26 for preventing inflow of air from the rod bore 16. The developer supply tube 20 is connected to pressurizing means 27 which forces the developer into the second passage 18 in the sampling valve 10 under high pressure.

A first fluid conduit 28 is connected to the cylinder 12 at a position in front of the piston 11, and a second fluid conduit 29 is connected to the same at a position to the rear of the piston. Both the conduits 28 and 29 extend into a control box 30 and are connected to the branched ends of a main fluid conduit 33 by way of a first electromagnetic valve 31 and a second electromagnetic valve 32 which are housed in the box 30. Used as the fluid is air at pressure of 3.5 to 7 kg/cm². The electromagnetic valves 31 and 32, when alternately opened and closed, reciprocally move the piston 11.

Figure 2:
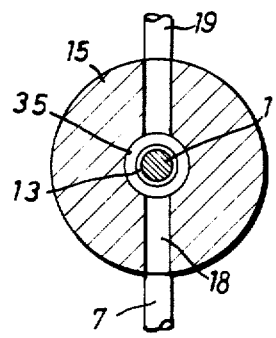
FIG. 2 is an enlarged view in section taken along the line II—II in FIG. 1.
Figure 3:
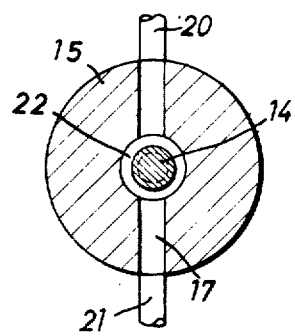
FIG. 3 is an enlarged view in section taken along the line III—III in FIG. 1.

At first, the piston 11 is held stopped in the solid-line position in FIG. 1. In this state, the withdrawing member 5 is placed in the receptacle 4 as indicated in the dot-and-dash line, and the pump 23 is operated to send the wash liquor into the first passage 17 through the tube 7 to purge the passage 17 and the annular groove 13 in the rod 14. The wash liquor flows out from the first passage 17 into the discharge tube 19 (see FIG. 2). When the purging procedure is completed, the withdrawing member 5 is shifted toward the cup 2, from which the member 5 picks up the sample. The sample is introduced through the tube 7 to the first passage 17 in the sampling valve 10. Upon the initiation of flow of the sample through the first passage 17, the first electromagnetic valve 31 is opened and, at the same time, the second electromagnetic valve 32 is closed, with the result that the fluid is forced into the cylinder 12 via the first conduit 28 to retract the piston 11, which in turn moves the rod 14 backward, with the sample accommodated in the space defined by the grooved surface 13 and the inner surface defining the rod bore 16. When the annular groove 13 is brought to the position where the rod bore 16 intersects the second passage 18 as indicated in the dot line in FIG. 3, the sample is guided into the annular groove 22 in the bore 16, then introduced to the second passage 18 and led through the tube 21 into the column 8. Due to the provision of the annular groove 22, the developer always flows through the second passage 18, via the tube 21 and into the column 8, even when the annular groove 13 is not positioned in the second passage 18. The developer carries the sample away from the annular groove 13, whereupon the first valve 31 is closed whilst the second valve 32 is opened at the same time. Thus the fluid is forced into the cylinder 12 via the second conduit 29. Consequently, the rod 14 advances, bringing its annular groove 13 to the position where the bore 16 intersects the first passage 17. At this time the same sample is still flowing through the first passage 17. When the valves 31 and 32 are switched as above, the control box 30 gives a signal 34 to the sampler 1, shifting the member 5 to the receptacle 4 and turning the table 3 a small amount to bring the next sample cup 2 to position. As in the beginning, the wash liquor picked up by the member 5 flows through the first passage 17 to purge away the preceding sample from the passage 17 and the annular groove 13 in the rod 14. When the purging procedure is completed, the withdrawing member 5 is shifted to the subsequent sample cup 2 to follow the same procedure as the previous one. The same operation as above is thereafter repeated. The control box 30 provides suitable settings for the sample pickup time, wash liquor pickup time, and the durations of movement and stopping of the piston 11 in the cylinder 12.

The chromatography apparatus incoporates a detector, and the values thereby detected are fed to a recorder 37 in the form of electric signals 36 and are recorded on a chart 38.

Experiments of quantitative determination were conducted employing the apparatus of this invention and using a solution containing sodium salt of cephalosporin C (herein referred to briefly as "CCNa") to compare the results with those obtained by conventional method.

A solution containing 0.5 mg/ml of CCNa was treated using the apparatus of this invention. A 10% aqueous solution of methanol was used as a wash liquor. The liquid sample was fed for 2 minutes and the wash liquor, for 3 minutes. The column of the liquid chromatographic apparatus was packed with Zipax SCX (trade name of cation-exchange resin manufactured by E. I. du Pont de Nemours & Co.) used as an adsorbent. The column was 50 cm in length and was used at a temperature of 30°C. As a developer, McIlvaine's buffer solution (mixed solution of citric acid and sodium secondary phosphate, pH: 2.5) was used. The apparatus of this invention was operated at column pressure of 30 kg/cm² (Experiment I according to this invention) and of 60 kg/cm² (Experiment II according to this invention). Further to conduct an experiment in a conventional manner, the sampling valve was manually operated to quantitatively determine CCNa in the CCNa containing solution (Conventional Experiment). The results obtained are given in the table below, in which $n$ represents the number of times, $\overline{X}$ the average height of peaks on the chart, SD standard deviaton and CV coefficient of variation, and $CV = SD/\overline{X} \times 100$.

|  | Conventional Experiment Height of peak | Experiment I Height of peak | Experiment II Height of peak |
|---|---|---|---|
| 1 | 18.71 cm | 18.95 cm | 12.66 cm |
| 2 | 18.54 | 19.17 | 12.69 |
| 3 | 17.24 | 18.96 | 12.70 |
| 4 | 14.00 | 19.00 | 12.76 |
| 5 | 13.75 | 19.08 | 12.51 |
| 6 | 13.66 | 19.15 | 12.69 |
| 7 | 13.20 | 19.15 | 12.65 |
| 8 | 13.53 | 19.06 | 12.71 |
| 9 | 13.05 | 18.97 | 12.66 |
| 10 | 17.92 | 19.20 | 12.72 |
| n | 10 | 10 | 10 |
| $\overline{X}$ | 15.36 | 19.07 | 12.68 |
| SD | 2.406 | 0.095 | 0.067 |
| CV | 15.7% | 0.50% | 0.52% |

The table shows that the apparatus of this invention gives data with very small fluctuations at a very high column pressure, making it possible to remarkably shorten the analysis time, and is therefore efficient to use.

What is claimed is:

1. An apparatus for liquid chromatography having an automatic sampling system comprising:
   an intermittently rotatable circular table means having a number of sample cups on its peripheral portion,
   a wash liquor receptacle disposed close to said circular table means,
   a withdrawing member means for being reciprocally movable between said wash liquor receptacle and one of said sample cups respectively brought to a specified position by said intermittent rotatable circular table means and then for being held in position for a specified period of time to withdraw the samples and the wash liquor alternately,
   a sample supply tube having the withdrawing member connected thereto,
   a sample discharge tube,
   a column including a column tube in communication therewith,
   a developer supply tube means for supplying developer,
   a pump means associated with said supply tube means
   a sampling valve comprising a hydraulic cylinder, a piston rod formed in its peripheral surface with an annular groove means for accommodating therein a definite amount of the sample, and a body fixed to a front end of said cylinder with said piston rod extending through said body, said body having an inner surface defining a rod bore slidably receiving said piston rod,
   parallel first and second passage means intersecting said rod bore and spaced apart from each other by a distance corresponding to a stroke of said piston rod, each of said passage means being in the form of a bore extending through said body and having a diameter smaller than the diameter of said piston rod, said first passage means for communicating with said sample supply tube at one end and with said sample discharge tube at the other end, said second passage means having one end communicating with said developer supply tube means and the other end communicating with said column tube in communication with said column, said inner surface of said body defining the rod bore being formed with a liquid passing annular groove at the intersection of said rod bore and each of said passage means.

2. An apparatus according to claim 1 wherein the pump is a proportioning pump.

3. An apparatus according to claim 1 wherein the supply tube is provided with a debubbler.

4. An apparatus according to claim 1 wherein the sample discharge tube is provided with a restrictor for preventing inflow of air from the rod bore.

5. An apparatus according to claim 1 wherein a wash liquor replenishing tube is connected to the wash liquor receptacle.

6. An apparatus according to claim 5 wherein the proportioning pump is associated with the wash liquor replenishing tube.

* * * * *